United States Patent [19]

Gokąbowski et al.

[11] 4,156,507

[45] May 29, 1979

[54] APPARATUS FOR REMOVING SAMPLES OF STREAM OF GRANULAR MATERIAL AND FOR PREPARING ANALYTICAL SAMPLES THEREFROM

[75] Inventors: Augustyn K. Gokąbowski, Swietochlowice; Gerard Kieltyka, Piekary Slaskie, both of Poland

[73] Assignee: Glowne Biuro Studiow I Projektow Przerobki Wegla Separator, Katowice, Poland

[21] Appl. No.: 846,207

[30] Foreign Application Priority Data

Nov. 5, 1976 [PL] Poland ............................ 193535

[22] Filed: Oct. 27, 1977

[51] Int. Cl.² ...................... B02C 21/00; B02C 25/00
[52] U.S. Cl. .................... 241/75; 73/423 R; 141/130; 241/81; 241/135
[58] Field of Search ................ 241/75, 81, 134, 135, 241/301, 24, 29; 73/423 R, 423 A, 452.2; 141/130, 124, 135, 137, 170, 175, 176; 198/568, 569; 222/358, 362

[56] References Cited

U.S. PATENT DOCUMENTS

| | | | |
|---|---|---|---|
| 1,186,646 | 6/1916 | Beekin | 73/423 R |
| 2,421,938 | 6/1947 | Held | 73/423 R |
| 2,495,944 | 1/1950 | Pletta et al. | 73/423 R |
| 2,738,679 | 3/1956 | Senkowski | 73/423 R |
| 3,252,328 | 5/1966 | Huntington | 73/423 R |
| 4,026,154 | 5/1977 | Pfeiffer et al. | 73/423 R |

*Primary Examiner*—Howard N. Goldberg
*Assistant Examiner*—Mark Rosenbaum
*Attorney, Agent, or Firm*—Haseltine, Lake & Waters

[57] ABSTRACT

Apparatus for removing samples from a stream of materials and for producing analytical samples therefrom comprising conveying a stream of granular material on a conveyor and discharging the material from the end of the conveyor through a hopper located in the path of the stream. The hopper occupies only a small portion of the width of the stream and the hopper is fixed to a plate which undergoes horizontal reciprocating motion transversely across the stream to vary the location at which the material enters the hopper. The height of the inlet of the hopper is at least as great as the thickness of the stream. The material separated by the hopper is conveyed through a chute to a crushing stage wherefrom an analytical sample of the desired size is obtained.

6 Claims, 3 Drawing Figures

… … …

APPARATUS FOR REMOVING SAMPLES OF STREAM OF GRANULAR MATERIAL AND FOR PREPARING ANALYTICAL SAMPLES THEREFROM

FIELD OF THE INVENTION

The invention relates to apparatus for taking samples from stream of a granular material, particularly coal, and for crushing the granular samples to produce an analytical sample.

PRIOR ART

Apparatus is known for taking samples of granular materials from a conveyor belt or from a stream of material moving continuously along a chute, trough or at pouring stations. Also known are crushing devices for preparing a laboratory sample of a grain size up to 6

The known method of preparation of a laboratory sample consists in crushing the primary sample taken to effect it's size reduction in one operation only to a size as required by the relevant standards in the spatial technological system. A receiver tester for implementation of this method consists of a stationary plate with a rectangular opening situated at the point of the falling material stream and an adjoining movable plate with a rectangular adjustable slot.

Such device renders possible partial removal of primary samples of granular materials from the cross section of the stream but does not ensure uniformity of the samples being taken in the case of systems of high capacity since the material being handled undergoes partial segregation on the conveyor as far as grain composition and specific gravity are concerned. This segregation combined with accumulation of material at the location of taking the samples does not guarantee separation of a representative primary sample from the entire cross section of the material being handled, the grains of which move along the pouring station with considerable speed mainly in the horizontal plane.

SUMMARY OF THE INVENTION

An object of this invention is to provide apparatus which overcomes the above-mentioned drawbacks and makes it possible to obtain a representative separation of a primary sample from the entire stream of the material being handled and provides preparation of an analytical sample of a grain size up to 0.1 mm. The apparatus is suitable, particulary, for coal.

The invention is applicable to granular materials within a broad range of grain classes at very large capacities and conveying speeds suited particularly for ports and loading stations of coal.

The apparatus for taking and preparing an analytical sample of a grain size up to 0.1 mm according to the invention consists in that the entire stream of material being handled is directed downward from the conveyor for further loading and passes through a movable plate periodically undergoing a reciprocating motion relative to it's horizontal axis, said plate being transversally disposed relative to the direction of the stream, said movable plate being provided with a through pocket or hopper located in the path of the stream of the material being handled which enables separation of a primary sample from the stream of the material being handled. The primary sample is next directed in accordance with the horizontal motion of the material to means for producing three-stage crushing with simultaneous size reduction in the first stage and return of the remaining material to the main loading system.

The final crushing operations are separated by the operation of drying of the separated analytical sample.

A receiver tester for implementation of the means according to the invention consists of at least one through pocket or hopper located in the path of the stream of the material being handled on a movable plate and fixed to this plate in an inseparable fashion. The movable, plate with the through pocket rests on a ball system and is guided in rollers. Stiffening of this movable plate is ensured by a distributing chute provided with adjustable power operated flaps with automatic control. Reciprocating motion of the said movable plate provided with the through pocket is effected by a driving system, preferably hydraulic, by remote control from a control panel.

The height of the inlet opening of the through pocket covers the entire thickness of the stream of the material being handled whereas the width of said opening is considerably smaller from the width of the stream. The cross section of the inlet opening of the through pocket is smaller than the cross section of the outlet opening. Such a solution ensures a laminar flow of the taken primary sample and minimizes possible jamming of the moist material, particularly coal.

The receiver tester according to this invention eliminates all disturbances encountered around the element for taking the primary samples and guarantees a representative taking of primary samples of granular materials, particularly coal, which is hard to transport and at very high capacities.

The taking of primary samples and the preparation of an analytical sample of a grain size up to 0.1 mm according to the invention is completely automated and controlled from a central control board of the plant and does not require additional personnel except a chief dispatcher.

BRIEF DESCRIPTION OF THE DRAWINGS

An embodiment of the invention is shown in the attached drawings, wherein.

DETAILED DESCRIPTION

Figure 1:
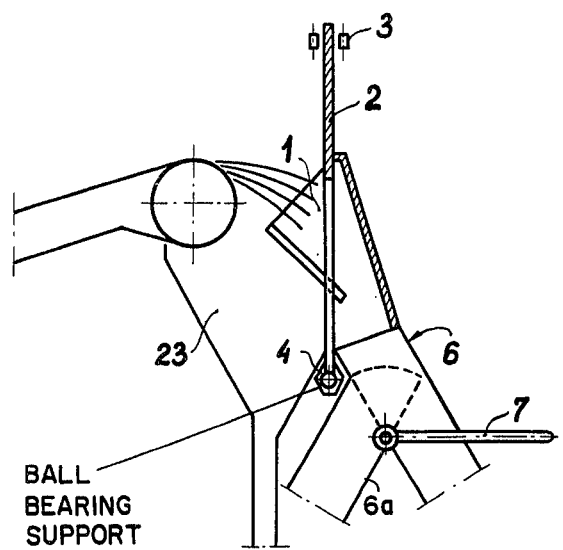
FIG. 1 is a cross section of the receiver-tester with a through pocket.
Figure 2:
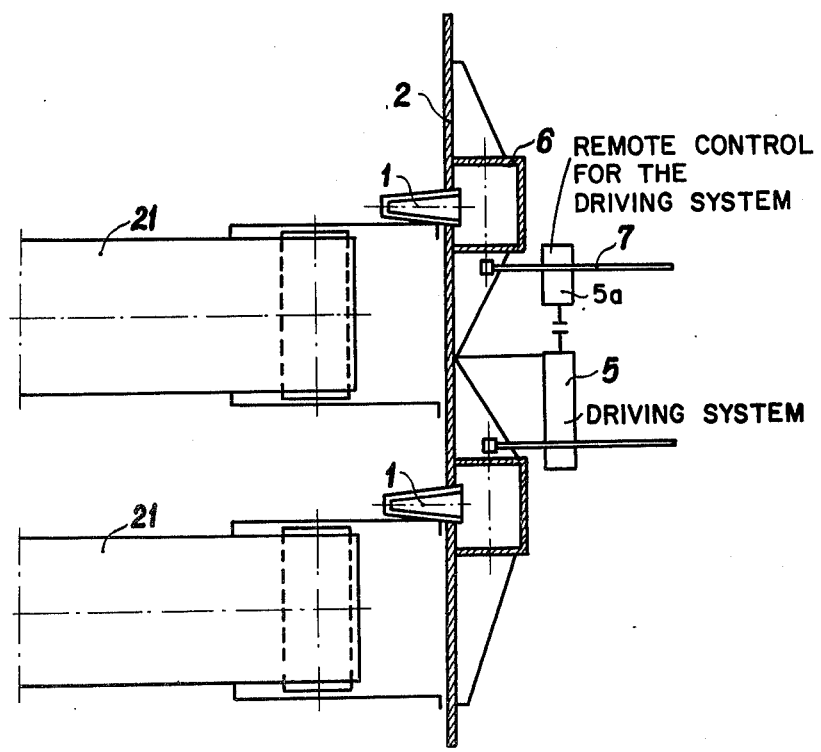
FIG. 2 is a top plan view of the apparatus in FIG. 1.
Figure 3:
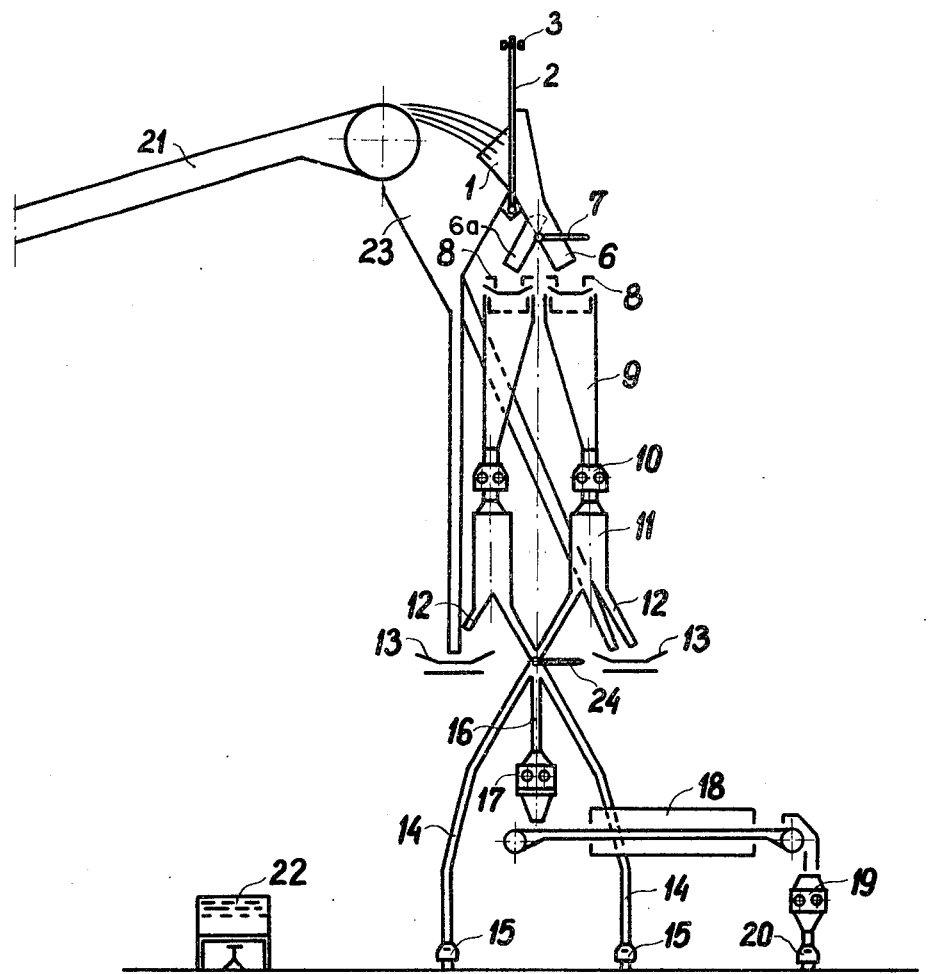
FIG. 3 is a diagrammatic showing of the system for preparation of an analytical sample.

The receiver-tester according to the invention consists of at least one through pocket or hopper 1 situated in the path of the stream of the material being handled, the pocket being secured on a movable plate 2 which performs periodically a horizontal reciprocating motion. Movable plate 2 is guided by rollers 3 and rests on ball bearing support 4. Reciprocating motion of movable plate 2 is effected by driving system 5 with remote control 5a, preferably hydraulic. On the other side of movable plate 2 in the direction through the outlet opening of the through pocket there is a distributing chute 6 provided with an adjustable chute 6a operated by a control rod 7, making it possible to divert the primary sample onto one of two belt conveyors 8, the chute 6 also stiffening the movable plate 2. The dimensions of the inlet of the through pocket 1 are dependent upon the cross section of the stream of the falling material, the height of said inlet opening being slightly greater than the thickness of the stream and the width of the opening being several times smaller than the width of said stream.

In the system for preparation of an analytical sample, according to the invention, there are provided special feeding chutes 9 under the conveyors 8, the outlets of the chutes being directed towards crushers 10 for preliminary crushing of the primary sample to a grain size up to 6 mm. Under the crushers 10 there are two size-reducing devices 11 which serve for separation of laboratory samples from the crushed primary sample whereas the remaining part of the material is conveyed by means of chutes 12 onto the main loading system 13. A laboratory sample separated in the size reducing device 11 can be conveyed either by means of chute 14 to containers 15 designed for storage of laboratory samples, or by means of chute 16 to crusher 17 for repeated crushing to a grain size of 3mm in crusher 17. The laboratory sample crushed in crusher 17 is conveyed through drier 18 to disintegrating unit 19 wherefrom the prepared analytical sample is conveyed to container 20 for storage of the analytical samples.

The preparation of the analytical sample according to the invention is effected as follows:

In the disclosed embodiment, two belt conveyors 21 designed for transport of granular material from a supply to final loading on loading conveyors 13 via chute 23 is used. In the path of the stream of the material being discharged from belt conveyor 21 there is disposed movable plate 2 with the through pockets designed for taking primary samples from one or both belt conveyors 21. The separated primary sample is conveyed through chute 6 or 6a by means of rod 7 onto belt conveyor 8. If the sample is taken simultaneously from two conveyors 21 then the adjustable chutes 6a are alternately operated so that the primary samples are supplied to both belt conveyors 8. In the case of taking one sample only from one arbitrary conveyor 21 this sample is directed onto one of the conveyors 8 and therefrom through chute 9 to crusher 10. The crushed material is conveyed to size reducing device 11, where the separation of the laboratory sample is effected and the remaining material is directed through chute 12 onto loading conveyor 13. The separated laboratory sample can be directed by means of chute 14 to conveyor 15 or by means of chute 16 to crusher 17 depending on the position of flap 24.

Material crushed in crusher 17 is conveyed to drier 18 and therefrom to disintegrating unit 19 and container 20 for storage of the individual analytical samples.

The entire technological process of taking and preparing samples of granular materials particularly coal, is controlled remotely from control board 22.

We claim:

1. Apparatus for preparing analytical samples from a stream of granular material comprising
    means for producing a stream of granular material of given width and thickness,
    sampling means including a hopper disposed in the path of said stream for separating a sample therefrom, said hopper having an inlet opening with a width corresponding to a small portion of the width of said stream and a height corresponding at least to the thickness of said stream,
    crushing means for receiving the sample separated by said hopper for producing an analytical sample,
    means for moving the hopper transversely across the stream to vary the location in the stream at which the material enters the hopper, said means comprising a plate fixedly supporting the hopper, and means rollably supporting said plate, and
    a distributing chute secured to said plate to receive sampled material discharged from the hopper, said distributing chute reinforcing said plate.

2. Apparatus as claimed in claim 1 wherein the width of the inlet opening of said hopper is several times smaller than the width of said stream.

3. Apparatus as claimed in claim 1 wherein the hopper has an outlet with a width greater than the width of the inlet opening.

4. Apparatus as claimed in claim 1 wherein the means for moving the hopper transversely further comprises means for moving said plate, hopper and chute as a unit in opposite directions transversely across said stream.

5. Apparatus as claimed in claim 4 further comprising a main control board with means for remote control of the speed of travel of the plate and the frequency of taking samples in the hopper.

6. Apparatus as claimed in claim 1 wherein said crushing means comprises a first crushing stage for crushing the sample and for returning a portion of the crushed sample back to the original stream.

* * * * *